United States Patent [19]

Negas et al.

[11] 4,264,423

[45] Apr. 28, 1981

[54] FLUIDIC THERMISTOR/FUGACITY DEVICE

[75] Inventors: Taki Negas, Ijamsville; Louis P. Domingues; Tadeusz M. Drzewiecki, both of Silver Spring; Richard M. Phillippi, Highland, all of Md.

[73] Assignee: The United States of America as represented by the Secretary of the Army, Washington, D.C.

[21] Appl. No.: 76,478

[22] Filed: Sep. 17, 1979

[51] Int. Cl.³ ............................................. G01N 27/46
[52] U.S. Cl. .................................. 204/195 S; 204/1 T
[58] Field of Search .............................. 204/1 S, 195 S

[56] References Cited

U.S. PATENT DOCUMENTS

| 3,468,780 | 9/1969 | Fischer | 204/195 S |
| 3,630,874 | 12/1971 | Olette et al. | 204/195 S |
| 3,738,341 | 6/1973 | Loos | 204/195 S |
| 3,767,469 | 10/1973 | Flais et al. | 204/195 S |

OTHER PUBLICATIONS

Sato, "Research Techniques for High Pressure and High Temperature", edit. by G. C. Ulmer, Chapt. 3, (1971), pp. 43–93.
Drzewiecki et al., "Fluidic Thermistor or Fluidic Temperature Sensing with Capillaries", Trans. ASME, Engineering for Power, vol. 99, No. 3, (1977), pp. 406–412.
Drzewiecki et al., "Fluidics-A New Potential for Energy Conservation by Continuous High Temperature Monitoring and Control", Heat Transfer in Energy Conservation, ASME, (1977), pp. 127–134.
Kiukkola et al., "J. Electrochem. Soc." vol. 104, (1957), pp. 379–387.
Fitterer, "J. Metals", Sep. 1967, pp. 92–96.

Primary Examiner—T. Tung
Attorney, Agent, or Firm—Nathan Edelberg; Robert P. Gibson; Saul Elbaum

[57] ABSTRACT

A device for measuring the fugacity of a material, without requiring a separate device to measure temperature, is disclosed, wherein the device is a solid electrolyte probe, with the probe having a passageway therein, and metallic conductor leads on the outside of the probe and on the inside of the probe in the passageway. The metallic conductor leads are in contact with an E.M.F. measuring circuit, with the reference fluid being passed through the passageway. The passageway also includes a capillary restriction therein, and measuring devices are provided to measure the pressure drop of the reference fluid when flowing through the capillary, thereby permitting determination of temperature. The temperature determination combined with the E.M.F. measurement permit determination of the fugacity of the material.

5 Claims, 4 Drawing Figures

FLUIDIC THERMISTOR/FUGACITY DEVICE

BACKGROUND OF THE INVENTION

Solid state sensors have been previously proposed by the art to measure the fugacity of various chemical species, such as, for instance, oxygen, sulfur and fluorine, in gases, liquids and solids at elevated temperatures. The oxygen fugacity sensor, sometimes simply called the oxygen sensor, is probably the most widely used of such solid state sensors. The foundation for the oxygen sensor was provided by K. Kiukkola and C. Wagner, J. Electrochem Soc. 104, 379 (1957). The use of the oxygen sensor for the rapid determination of oxygen in liquid steels, in the steel making process, is described in *J. Metals*, G. R. Fitterer, September, 92 (1967).

A general review of solid electrolyte fugacity sensors for oxygen and other gases is described in *Research Techniques for High Pressure and High Temperature*, M. Sato, edit. by G. C. Ulmer, Chapt 3, Springer-Verlag, New York 1971, p. 367.

Typically oxygen sensors consist of a ceramic solid state electrolyte (>99% oxygen ion conductivity) such as zirconia doped with CaO or $Y_2O_3$. Ceramics are fabricated as closed- or open-end tubes or as dense, thin discs. Opposed surfaces are metallized (e.g. with Pt, Au, Ag, etc.) and metal leadouts measure an open-circuit voltage according to, $$E \text{ (millivolts)} = 0.0496\ T(K) \log \frac{f_{O_2} \text{ (reference)}}{f_{O_2} \text{ (unknown)}}$$

Temperature (generally, T>673 K), is measured independently, typically by thermocouples positioned adjacent to the sensing (presumably isothermal) portion of the cell either internally or externally. A reference, known $f_{O_2}$ [e.g. air ($f_{O_2} = 0.21$ atm) or oxygen ($f_{O_2} - 1$ atm)] is provided to one of the surfaces of the sensor. With T(K), $f_{O_2}$ (reference), and a measured voltage E, $f_{O_2}$ (unknown) can be calculated.

For many years researchers have used oxygen sensors not only to monitor and control the fugacity of oxygen in gas mixtures but to measure chemical equilibria associated with solid-liquid-gas redox reactions. Subsequently, industry has developed probes to control fuel/air combustion for large glassmaking furnaces, to monitor exhaust gases from automobiles, and to determine the oxygen content of molten metals in metallurgical processes. Numerous other industrial applications related to measurement and control of combustion processes will develop in the future.

Measurement of temperatures (T(K) in equation 1) necessary for laboratory and industrial measurements of oxygen fugacity has been generally limited to methods related to, (1) mechanical/expansion, (2) the Seebeck-Peltier effect (thermocouples), (3) electrical resistivity, and (4) optical pyrometry.

Recently, proposals have been made to utilize fluidic temperature sensing methods, based upon change of the fluid properties, such as viscosity, density, etc., with temperature. A tube fabricated from an inexpensive ceramic ($Al_2O_3$, $MgAl_2O_4$(spinel), $ZrO_2$) can be the temperature probe. The fluidic capillary thermometer operates on a very small flow of fluid (e.g., $10^{-6}\ m^3$/sec for air) provided through an interior channel. At the "hot" or sensing end, the channel is reduced to a capillary flow resistance which can be described with the following relationships, $$R = (\Delta P)/Q = C\mu = f(T)$$

where
R = flow resistance
$\Delta P$ = pressure drop across capillary
Q = volumetric flow rate
$\mu$ = absolute viscosity
T = temperature
C = constant for a given probe Resultant changes in pressure drop due to changes in viscosity, and hence, temperature, are then amplified to a usable level by inexpensive, low-noise, laminar fluidic pressure amplifiers. Ultimately, a pressure output directly as a function of temperature is provided.

To provide a local temperature measurement, the capillary is made very small and short, typically about 2 cm long and 0.5–0.75 mm in diameter. A fluidic circuit, incorporating biasing resistors and a fluidic amplifier all operating with the working fluid, is used to provide temperature output reading. The sensor is merely a variable resistor in a bridge network and is well known in the art as demonstrated in the literature by Drzewiecki, T. M. and Phillippi, R. M., "Fluidic Thermistors or Fluidic Temperature Sensing with Capillaries," Trans. ASME, *Engineering for Power*, Vol. 99, No. 3, July 1977 and Drzewiecki, T. M., Phillippi, R. M., and Paras, C. E., "Fluidics—A New Potential for Energy Conservation by Continuous High Temperature Monitoring and Control," *Heat Transfer in Energy Conservation*, ASME, 1977.

The output pressure differential is proportional to the temperature of the gas flowing through the capillary and may be read out on a pressure gage or with an electronic transducer. Typically with a gage, accuracy of $\pm 1°$ C. may be expected. Greater accuracy is obtainable with a transducer due to the ability to expand the scale. Readings to $\pm 0.01°$ C. would not be unreasonable with a transducer.

SUMMARY OF THE INVENTION

The present invention is directed to a device for measuring temperature and fugacity of a material, such as a gas, and especially of oxygen. The device includes a solid electrolyte probe which is conductive to ions of the material, thermally stable and chemically inert to the material, and has a low permeability to neutral materials and other ions. The probe contains a passageway for flow of a reference fluid therethrough, and the passageway contains a capillary restriction forming a fluidic thermistor. Metallic conductor leads are provided on the outside of the probe exposed to the material, and on the inside of the probe in the passageway, generally reasonably close to the capillary restriction and generally opposite the outside conductor lead, and forming together with the solid electrolyte and the reference fluid a solid electrolyte sensor. As an alternative construction, when the material in contact with the outside of the solid electrolyte probe is a molten metal, or similar material, the outer conductor lead may be eliminated, with the molten metal itself serving as the conductor lead. The conductor leads are part of a circuit for measuring the E.M.F. between the leads, and conventional solid electrolyte sensor circuitry may be used between the leads.

Pressure drop measurements involving the capillary restriction permit determination of temperature, and the E.M.F. measurement together with the determined temperature permits the determination of the fugacity of the material outside of the probe.

The device of the present invention provides numerous advantages. The need for independent pyrometric- or thermocouple-based methods of temperature measurement are obviated. Interfacing with control hardware can be simplified at low cost without loss of precision and accuracy. The cell can be calibrated in a very simple manner. Less sealing problems will be encountered, if, for instance, the probe is to be inserted into or on the side of a vessel containing material under high pressure. For vessels or pipes having contained material at high flow rates, less flow interruption will be encountered with the device of the present invention, as compared to the use of two separate probe devices in the prior art. The measurement of temperature and E.M.F. can be essentially at the same point, thereby obviating the effects caused by non-uniform conditions in the vessel, container or pipe holding the material to be measured.

DETAILED DESCRIPTION OF THE INVENTION

Figure 1:
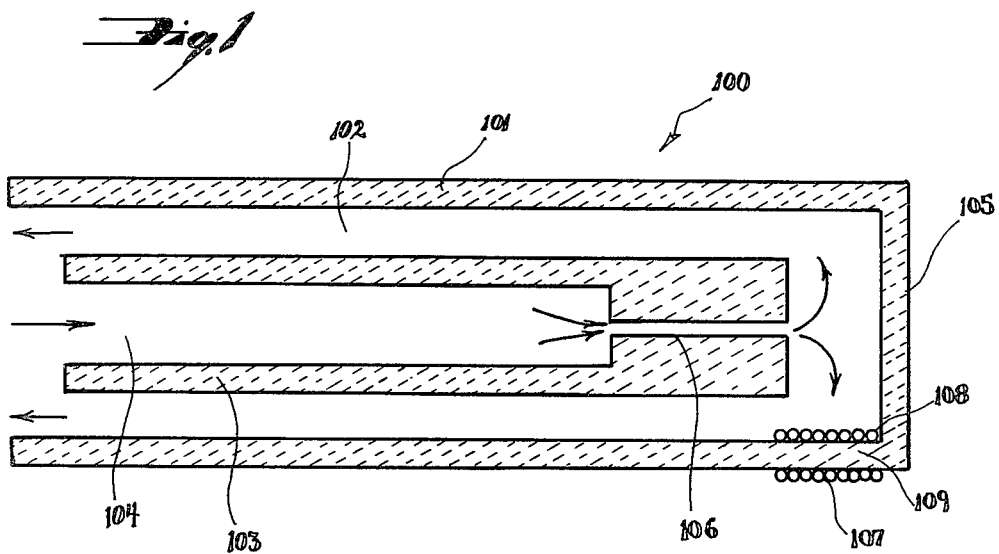
FIG. 1 is a cross-sectional view of a solid electrolytic probe of the present invention, with the circuitry omitted for clarity.

In FIG. 1, sensor 100 is illustrated in the form of an elongated probe member 101 having an internal passageway 102 therein. Inside of passageway 102 is a movable ceramic tube 103 having an internal passageway 104 therein. End 105 of probe 101 will be exposed to the material of unknown fugacity which is to be measured, and passageway 104 terminates in a capillary 106 in tube 103.

The capillary 106 is of such a size, compared to passage 104, that laminar flow (that is, non-turbulent flow) will be encountered in capillary 106 during conditions of normal operation. The variables with respect to obtaining the desired laminar flow include the respective lengths and diameters of passage 104 and capillary 106, as well as the flow rate of gas introduced into passageway 104 at the end opposite probe end 105 (the flow of the reference fluid is shown by arrows). It is most important that the ratio of the diameters of passageway 104 and capillary 106 be such that the diameter of passageway 104 is at least 10 times greater than the diameter of capillary 106. It is preferred that the length of passageway 104 be at least 10 times greater than the length of capillary 106. Normally a fluid flow regulator will be placed just upstream of passageway 104 to ensure a uniform supply of the reference fluid to the fluidic thermistor, but it will be readily appreciated by those in the art that the fluid flow regulator could be placed further upstream, thereby lengthening the effective length of passageway 104.

Reference fluid flowing through capillary 106 is discharged into that portion of passageway 102 adjacent the end 105 of the probe, and reverses its flow to flow away from end 105 through passageway 102, as shown by the arrows.

As the temperature determination depends upon the viscosity of the fluid flowing through capillary 106, it is important that the capillary 106 be exposed to the temperature of the material (the temperature of which is to be measured) surrounding the outside of probe 101, so that the fluid flowing through capillary 106 will be substantially at the temperature of the material being measured.

Metallic conductor lead 107 is plated or otherwise placed in position to wet-out the solid electrolyte of which tube 101 is made. Metallic conductor lead 108 is likewise plated inside of passage 102 and opposite metallic lead 107, forming an area 109 of solid electrolyte thereinbetween. For accurate measurements of fugacity, it is greatly preferred that the metallic lead 108 be proximate capillary 106.

Metallic conductor lead 107 and metallic conductor lead 108 are connected by wires (not shown) or other means to a simple potentiometer, or other means of measuring the E.M.F. therebetween.

The pressure drop caused by passage of the reference fluid through capillary 106 can be measured several ways, as is conventional in the art. Pressure transducers can be located immediately upstream and immediately downstream of capillary 106. However, it is much easier and greatly preferred to simply measure the back pressure of the reference fluid at a point upstream of capillary 106. The simplest way of measuring the back pressure would be through a simple pressure gage, but other means can of course be utilized.

Tube 103 can be of any convenient ceramic or other material which will withstand the temperatures to which the sensor will be exposed, and which will not contaminate the reference fluid passing therethrough, and will exhibit good dimensional stability. Ceramic materials are generally preferred. Tube 103 can be movable through adjustment means (not shown) so as to optimize the location of tube 103 in probe 101.

Sensor 100 is illustrated in the form of a probe, but it will be readily appreciated that the sensor can be a flush-mounted sensor, so that no elongated probe is required. All that is important is that the metallic lead 107 be exposed to the material to be measured, and the reference fluid flowing through capillary 106 be substantially at the temperature of such material.

There is no real upper limit as to the size of the diameter of probe 101, but it will be readily appreciated that large sizes might cause more fluid flow interruption, might function as heat sinks so as to require substantial times of exposure to a given temperature before reaching equilibrium, may be more subject to thermal shock effects, and certainly would be more costly. For these reasons, then, the probe will generally be of a relatively small diameter, generally less than 1 inch in diameter.

Probe 101 will be made of a solid electrolyte material, and this material can be of any of the various solid electrolytes known to the art as suitable solid electrolyte sensors. The various materials discussed in the above-referenced Sato paper, the disclosure of which is hereby incorporated by reference, can be utilized for the solid electrolyte. The preferred solid electrolyte is a zirconia material which has been doped with 8 to 20 weight percent of yttria, preferably about 17 weight percent of yttria. Normally the thickness of solid electrolyte material between the metal leads will be about 50 to 200 mils, and it will be readily appreciated that the wall thickness of probe 101 should be as thin as possible, to permit rapid heat transfer therethrough, as long as the wall thickness is such as to preclude interfering passage of neutral gases and ions of other materials.

The metallic leads are preferably of platinum, although the most suitable metallic lead will vary depending upon the particular application, as is known to the art. For instance, the Sato paper acknowledged above discloses suitable metallic leads for various applications, and is incorporated herein by reference for such additional disclosure as well. The metallic leads can be of any desired thickness as long as they are still capable of rapidly passing ions of the material being measured therethrough.

The capillary 106 may typically have a length of 2 cm and a diameter of 0.5 to 0.75 mm. These dimensions are typical, but can vary from these typical dimensions, as is well known to those in the art. It is important that the pressure drop across the capillary be of a magnitude which is readily determinable at the expected temperatures, and the pressure drop will vary in direct proportion to the length of the capillary, and in inverse proportion to the radius of the capillary to the fourth power. With these design parameters, then, it is readily within the skill of those in the art to select suitable combinations of diameter and length of the capillary.

Likewise, the diameter and length of the passageway upstream of the capillary can vary widely, depending upon the dimensions chosen for the capillary itself. It is important that the diameter of the passageway be at least 10 times greater than that of the diameter of the capillary, and the length of the upstream passageway is preferably at least 10 times that of the length of the capillary.

The dimensions of the passageway downstream of the capillary are less critical, but the diameter thereof should generally be of the same order of magnitude as the diameter of the upstream passageway, or of greater diameter.

Another way of referencing the interrelationship of the dimensions of the upstream passageway and the capillary is that the upstream passageway should have a fluid resistance which is at least 100 times less than the fluid resistance of the capillary.

For the case of using a cheap, disposable reference fluid such as air, the reference fluid can be simply discharged to atmosphere following passage through passageway 102. Alternatively the reference fluid could be cooled and recycled to the sensor device.

Figure 2:
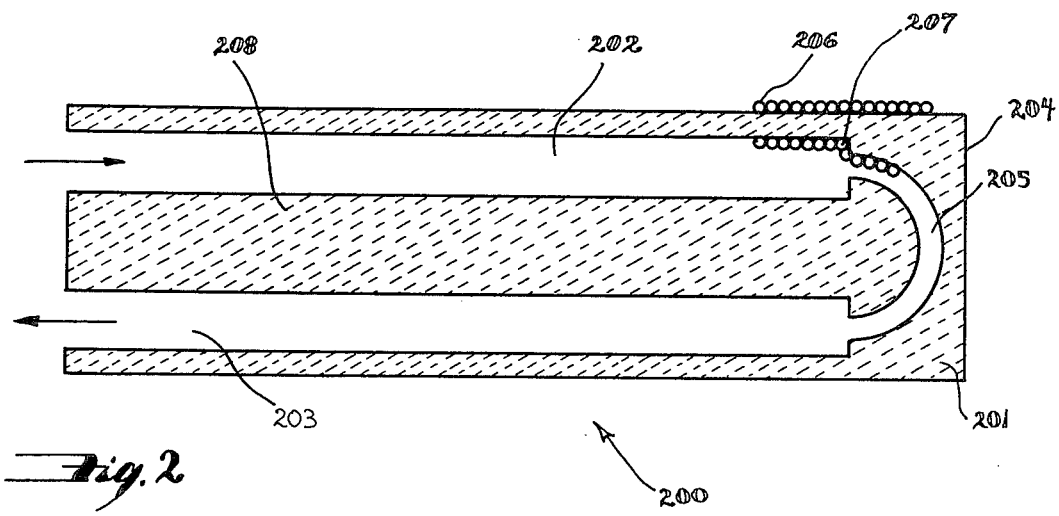
FIG. 2 is a cross-sectional view of an alternative sensor of the present invention, with circuitry omitted for clarity.

FIG. 2 is generally similar to FIG. 1, but of monolithic construction. FIG. 2 illustrates a sensor 200 which includes a probe 201 having an inlet port 202 and an outlet port or passageway 203 therein. End 204 of probe 201 is exposed to the material to be measured. The ends of passageway 202 and passageway 203 adjacent end 204 are connected by capillary 205. External lead 206 and internal lead 207 are mounted adjacent capillary 205, with internal lead 207 located in upstream passageway 202. The central section 208 of probe 201 is integral with the rest of the probe and thus this sensor 200 is not adjustable in the manner of the sensor of FIG. 1. Other than this, the function and operation, as well as the general dimensions, of the probe of FIG. 2 are generally similar to that described hereinabove for the sensor of FIG. 1.

Figure 3:
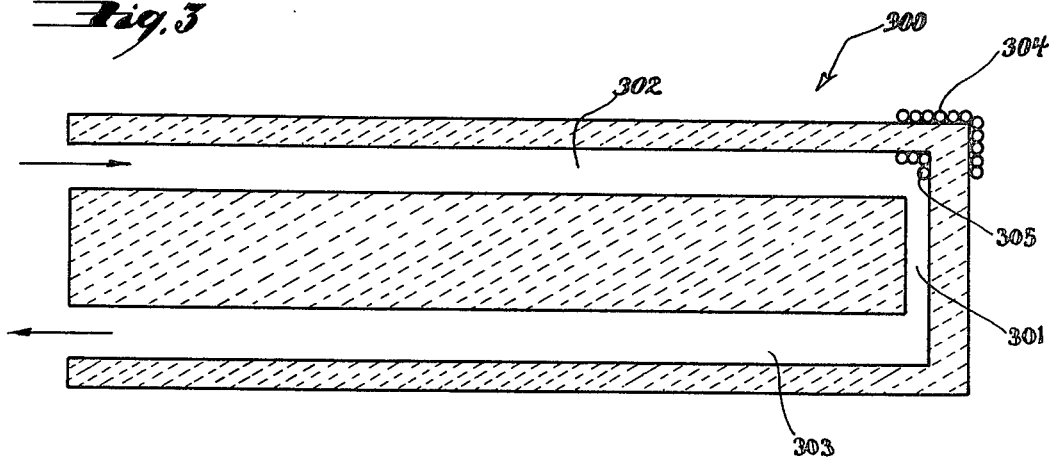
FIG. 3 is a cross-sectional view of another sensor of the present invention, with circuitry omitted for clarity.

FIG. 3 illustrates a sensor 300 which is similar to the sensor 200 of FIG. 2, except that capillary 301 extends in a straight rather than a curved path between the end of upstream passageway 302 and downstream passageway 303. Electrodes 304 and 305 are of different configurations, and in a somewhat different location. Other than this, the sensor 300 is identical to the above-described sensor 200 of FIG. 2.

Figure 4:
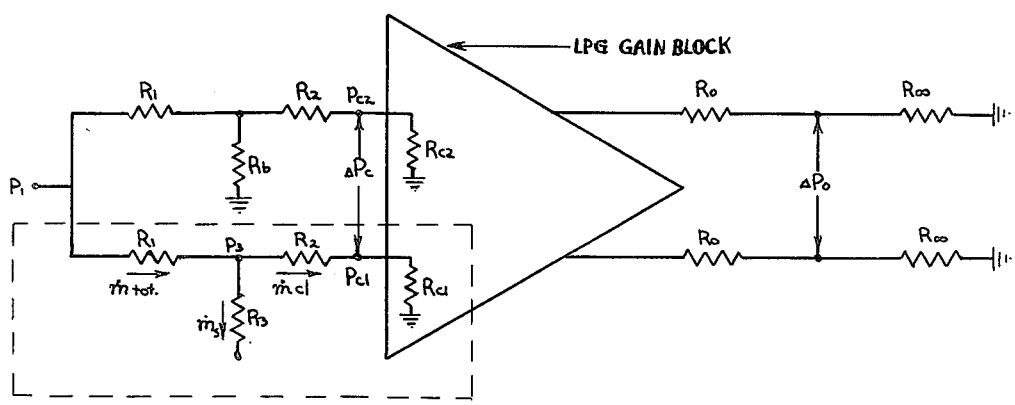
FIG. 4 is a schematic circuit diagram of a suitable circuitry to be used in the fluidic thermistor portion of the device of the present invention.

In FIG. 4, a simplified block diagram is illustrated. The pressure drop $\Delta P_c$ is the pressure differential between the sensor and a biased resistor and is amplified to produce the amplified pressure drop value $\Delta P_o$. The amplification is by way of conventional low noise fluidic amplifiers, which are well known to those in the art.

The device of FIG. 1 was used in early experimentation involving the development of the sensor of the present invention. The device of FIG. 2 is currently utilized, and it is anticipated that the ultimate design may be somewhat more similar to that of FIG. 3.

It is preferred that the metallic leads on the outside of and interior of the sensor be of the same metals, so that no parasitic E.M.F.'s will be formed thereinbetween. Dissimilar metals can be used, however, as long as appropriate corrections to the measured E.M.F. values are made.

The solid electrolyte fugacity sensors utilized to date have generally been oxygen sensors, but it is known that those in the art are developing sensors to detect the fuguacities of other gases, such as fluorine, chlorine, sulfur, etc. No reason is now seen why the sensor of the present invention cannot be used to similarly measure the fugacities of such other gases. Appropriate design modifications will have to be made, such as, for instance, the use of different solid electrolytes when necessary for the measurements of other gases. For instance, when measuring the fugacity of fluorine, it is likely that the solid electrolyte would be lanthanum trifluoride.

The reference fluid is preferably a gas, and may be any of the gases disclosed in the aforesaid Sato publication, the disclosure of which has already been incorporated herein by reference. For measuring the fugacity of oxygen, it is generally preferred to utilize air or pure oxygen as a reference gas, and the use of air is most preferred for normal operations.

The sensor device of the present invention may be used in any of the applications wherein the prior art previously used the separate solid electrolyte sensors and temperature measuring devices, including process industries, vehicular exhaust systems, monitoring and control of jet engine combustion, combustors, glass and steel making furnaces, sophisticated preheaters for magneto hydrodynamic processes, gasifiers, boilers, and the like. The main utility of the present device resides in the ability to measure both E.M.F. (and, after appropriate calculations, fugacity) and temperature simultaneously, and at locations which are quite close to one another. Thus, inaccuracies in the measurements caused by localized variables in either fugacity or temperature can be essentially eliminated, so that more accurate readings are obtained. It will be readily appreciated that the reference gas or other fluid used in the solid electrolyte sensor portion of the present device also functions as the working fluid of the fluidic thermistor, and thus while leading to higher accuracy greatly simplifies the apparatus required.

The Fitterer publication described hereinabove discloses certain disposable oxygen sensor tips for use in steel making processes, and it will be clear that the devices of the present invention can use such disposable tips.

One of the problems which have faced the fluidic thermistors of the prior art is the calibration of the devices to equate a pressure change reading to a given temperature. The present invention eliminates this difficult calibration step by permitting calibration of the temperature through the solid electrolyte fugacity sensor portion of the present development. That is, when two known gases, for instance, are chosen as the reference and unknown gases (for instance, air as the reference gas and pure oxygen as the unknown gas), then the first equation set forth in the section of the present specification titled "Background of the Invention" reduces to a simple equation of $E(\text{millivolts}) = T(K) \times$ a constant. The T(K) value can be readily calculated upon measuring the E.M.F. across the solid electrolyte sensor, with the air/oxygen or other known gases on either side of the solid electrolyte. A $\Delta P$ reading taken at the same time as the E.M.F. reading permits a point to be determined on the pressure change vs. temperature curve. Two such determinations utilizing temperatures which are different but still reasonably close to one another (i.e., within a couple of hundred degrees K of each other) will provide reference points on the calibration curve, and permit $\Delta P$ measurements to be converted into temperature determinations with reasonable levels of accuracy, utilizing this very simple calibration procedure.

Other advantages of the device of the present invention are readily apparent from the above description and accompanying drawings. These advantages include simplicity of design, the lack of moving parts, the continuous purging of the internal portion of the sensor by the reference gas, and the possibility to operate at temperatures or environments where other temperature measuring devices are subject to high failure rates. The device of the present invention should exhibit extremely high reliability provided that suitable materials of construction are chosen for the particular environment in question.

In many applications, especially those involving high velocity fluids, it is most important to keep any probes or other devices which cause fluid turbulence to a minimum, and the present device permits a single probe to be utilized in applications wherein the art at times had to utilize two separate probe devices.

While the sensor of the present invention is preferably in an elongated probe form, it will be readily appreciated that for certain applications, such as measurements in the throat of a jet engine, the device may be of a flush-mount design, as mentioned hereinabove.

While the reference above to the metallic electrode attached to the solid electrolyte has been with reference to the term "metallic conductor lead," it is to be understood that it is the electrode area itself not the wire leads leading from the electrode to suitable measuring devices that is meant.

What is claimed is:

1. Device for measuring temperature and fugacity of a material, said device comprising a solid electrolyte sensor, which electrolyte is conductive to ions of said material, thermally stable and chemically inert to said material, and has low permeability to neutral materials and other ions, a passageway for a reference fluid in said sensor, said passageway including a capillary restriction which is of a cross-sectional area no greater than one-tenth the area of the remainder of said passageway so as to produce non-turbulent flow therein, a first metallic conductor lead on the outside of the sensor and exposed to said material, a second metallic conductor lead on the inside of the sensor in said passageway generally proximate said capillary restriction and generally opposite said first lead, said leads in contact with said solid electrolyte therebetween, chemically inert to, non-contaminating to and not appreciably miscible with said material and said electrolyte and having a high melting point and low vapor pressure, electromotive force measuring means electrically connected to said leads to measure the E.M.F. therebetween, and pressure drop means to measure the pressure drop of the reference fluid when flowing through said capillary, whereby the pressure drop measurement permits determination of temperature of said material, and said E.M.F. measurement together with said determined temperature permits determination of the fugacity of said material.

2. Device of claim 1, wherein said sensor is elongated, and said passageway extends along the length thereof.

3. Device of claim 1, wherein the fluid resistance of the capillary is at least 100 times greater than the fluid resistance of the passageway upstream of the capillary.

4. Device of claim 1, wherein the passageway upstream of said capillary is at least 10 times as long as the length of said capillary.

5. Device of claim 1, wherein each of the metallic conductor leads, or fugacity sensor electrodes, are of the same metal.

* * * * *